US00PP20946P2

(12) United States Plant Patent
van Kleinwee

(10) Patent No.: US PP20,946 P2
(45) Date of Patent: Apr. 27, 2010

(54) ***PETUNIA* PLANT NAMED 'PETVANI'**

(50) Latin Name: *Petunia hybrida*
Varietal Denomination: Petvani

(75) Inventor: Theodorus Cornelis Maria van Kleinwee, Hoorn (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/321,673

(22) Filed: Jan. 23, 2009

(51) Int. Cl.
*A01H 5/00* (2006.01)

(52) U.S. Cl. ..... Plt./356

(58) Field of Classification Search ..... Plt./356
See application file for complete search history.

*Primary Examiner*—Susan B McCormick Ewoldt
(74) *Attorney, Agent, or Firm*—S. Matthew Edwards

(57) ABSTRACT

A new *Petunia* plant named 'Petvani' characterized by its trailing, outwardly spreading plant habit, very strong branching habit, very floriferous habit, single flowers that are vanilla in color, and good garden performance.

1 Drawing Sheet

Latin name of the genus and species of the plant claimed: *Petunia hybrida.*

Varietal denomination: 'Petvani'.

BACKGROUND OF THE NEW PLANT

The present invention relates to a new and distinct cultivar of *Petunia* plant, botanically known as *Petunia hybrida*, and hereinafter referred to by the cultivar name 'Petvani'.

The new *Petunia* is a product of a planned breeding program conducted in Enkhuizen, Netherlands. The new *Petunia* cultivar has a trailing and spreading plant habit and big vanilla colored flowers.

The new *Petunia* originated from a cross between a *Petunia hybrida* seedling selection as the female, or seed, parent identified as 'B0896-1,' and a *Petunia hybrida* seedling selection as the male, or pollen, parent identified as 'A0982-1.' This cross was made in August 2003. The new *Petunia* was discovered and selected as a single flowering plant within the progeny of the stated cross in May 2004.

Asexual reproduction of the new cultivar by terminal cuttings at Enkhuizen since August 2004, has shown that the unique features of this new *Petunia* are stable and reproduced true to type in successive generations.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

SUMMARY OF THE INVENTION

The following traits have been repeatedly observed and are determined to be the unique characteristics of 'Petvani'. These characteristics in combination distinguish 'Petvani' as a new and distinct cultivar:

1. Spreading plant habit
2. Very strong branching
3. Very floriferous

4. Vanilla colored flowers
5. Very strong heat tolerance

In side-by-side comparisons conducted in Enkhuizen, Netherlands, plants of the new *Petunia* differed from plants of the female parent selection in the following characteristics:

1. Plants of the new *Petunia* have a stronger heat tolerance than the plants of the female parent.
2. Plants of the new *Petunia* are more branched than plants of the female parent.

In side-by-side comparisons conducted in Enkhuizen, Netherlands, plants of the new *Petunia* differed from plants of the male parent selection in the following characteristics:

1. Flowers of the new *Petunia* open up wider than flowers of the male parent.
2. Plants of the new *Petunia* flower earlier than plants of the male parent.

TABLE 1

DIFFERENCES BETWEEN THE NEW CULTIVAR 'PETVANI' AND A SIMILAR CULTIVAR

| | 'Petvani' | 'Petpasyel' (U.S. Plant Pat. No. 18,720) |
|---|---|---|
| Heat tolerance | Very strong (foliage stays green under hot conditions) | Weak (foliage turns yellow under hot conditions) |
| Branching | Very strong | Weak |
| Flower shape | Flower opens completely | Flower does not open completely |

DESCRIPTION OF THE NEW CULTIVAR

The observations and measurements describe plants grown in Enkhuizen, Netherlands, in week 23, 2008 in hanging baskets on the trial field in Enkhuizen, on plants of approximately 13 weeks old.

In the following description, color references are made to The Royal Horticultural Society Colour Chart, 2001 Edition, except where general terms of ordinary dictionary significance are used.

The plant:

*Classification—botanical.—Petunia hybrida.*

Parentage:

*Female parent.—Petunia hybrida* selection 'B30896-1,' not patented.

*Male parent.—Petunia hybrida* selection 'A0982-1,' not patented.

Propagation:

*Type.*—Terminal cuttings.

*Time to initiate roots.*—7 days.

*Time to develop roots.*—14 days.

*Root description.*—Fine, fibrous, white in color.

*Rooting habit.*—Freely rooting.

Plant description:

*Shape.*—Annual flowering plant; indeterminate; initially upright, later on more trailing and outwardly spreading. Strong branching habit; about five basal branches each with 7 to 10 lateral branches. Pinching enhances development of lateral branches, but is not necessary to create a well filled plant.

*Usage.*—Appropriate for hanging baskets, window boxes, patio containers and landscape applications.

*Plant height* (*from soil level to top of plant plane*).—10 cm.

*Plant diameter* (*area of spread*).—60 cm.

*Vigor.*—Strong.

*Lateral branches.*—Length: 30 cm Diameter: 4 mm Internode length: 3 cm Texture: Canescent Color: 144A The foliage:

*Arrangement.*—Opposite, decussate, sessile, simple.

*Length.*—4–5 cm.

*Width.*—2 cm.

*Shape.*—Lanceolate.

*Apex.*—Acuminate.

*Base.*—Attenuate.

*Margin.*—Entire, slightly ciliated.

*Texture, upper and lower surface.*—Sparsely pubescent.

*Venation.*—Pinnate.

*Color.*—Developing foliage, Upper surface: 137B. Lower surface: 137C. Fully expanded foliage, Upper surface: 137C. Veins upper surface: 146C. Lower surface: 146B. Veins lower surface: 146C.

*Petiole.*—Length: 0.5–2 mm. Diameter: 1.5 mm. Color, upper and lower surface: 146C. Texture: pubescent.

The flower:

*Flower type and habit.*—Single funnel-shaped flowers, slightly rotate. Flowers face mostly upward and outward; axillary. Floriferous habit, three to five open flowers and about three flower buds per lateral branch at a time.

*Natural flowering season.*—Continuous flowering from spring until frost in the autumn.

*Flower longevity on the plant.*—6 days.

*Fragrance.*—Strong.

*Flower size.*—Diameter: 7 cm. Tube length: 3 cm. Throat diameter, distal end: 1.3 cm. Tube diameter, proximal end: 3 mm.

*Flower buds.*—Length: 4.8 cm. Diameter: 9 mm. Shape: Elongated oblong with ruffled apices Color: 145C with veins 145A; at apex 145 C

*Petals.*—Quantity/arrangement: Five petals fused in a single whorl, funnel shaped, slightly rotate. Width: 3.3 cm. Shape: Spatulate. Apex: Rounded. Margin: Entire. Texture, upper and lower surface: Smooth, velvety. Color When opening, upper surface: 157D, veins 145A. When opening, lower surface: 157D, veins 145A. Fully opened, upper surface: 157D, veins 145B. Fully opened, lower surface: 157D, veins 145A. Flower throat (inside): 157D, veins 145A. Flower tube (outside): 157D, veins 145A.

*Sepals.*—Arrangement/appearance: Single whorl of five sepals fused at base, rotate shape. Length: 1.5 cm. Width: 4 mm. Shape: Ligulate. Apex: Rounded. Margin: Ciliated. Texture, upper and lower surface: Puberulous. Color, upper surface: 137B. Color, lower surface: 137C.

*Peduncles.*—Length: 3.5–6 cm. Width: About 1.5 mm. Angle: 40° to 70° from the stem. Strength: Strong. Texture: Puberulous Color: 143B.

Reproductive organs:

*Stamens, quantity per flower.*—5.

*Anther shape.*—Two-parted, round, ends fused.

*Anther length.*—3 mm.

*Anther diameter.*—2 mm.

*Anther color.*—155A.

*Pollen amount.*—Large.

*Pollen color.*—155A.

*Pistils, quantity per flower.*—1.

*Pistil length.*—2.0–2.5 cm.

*Style length.*—1.8–2.0 cm.

*Style color.*—144D.

*Stigma shape.*—Ovate.

*Stigma color.*—143A.

*Ovary color.*—143A.

Seed development:

Seed development and/or fruit production has not been observed to date.

Disease and pest resistance:

No disease and pest resistance has been observed to date.

Garden performance:

Plants of the *Petunia* named 'Petvani' have been observed to have good garden performance. They have been noted to tolerate rain, wind and temperatures from 2 to 39 degrees C.

What is claimed is:

1. A new and distinct cultivar of *Petunia* plant named 'Petvani', as substantially illustrated and described herein.

* * * * *

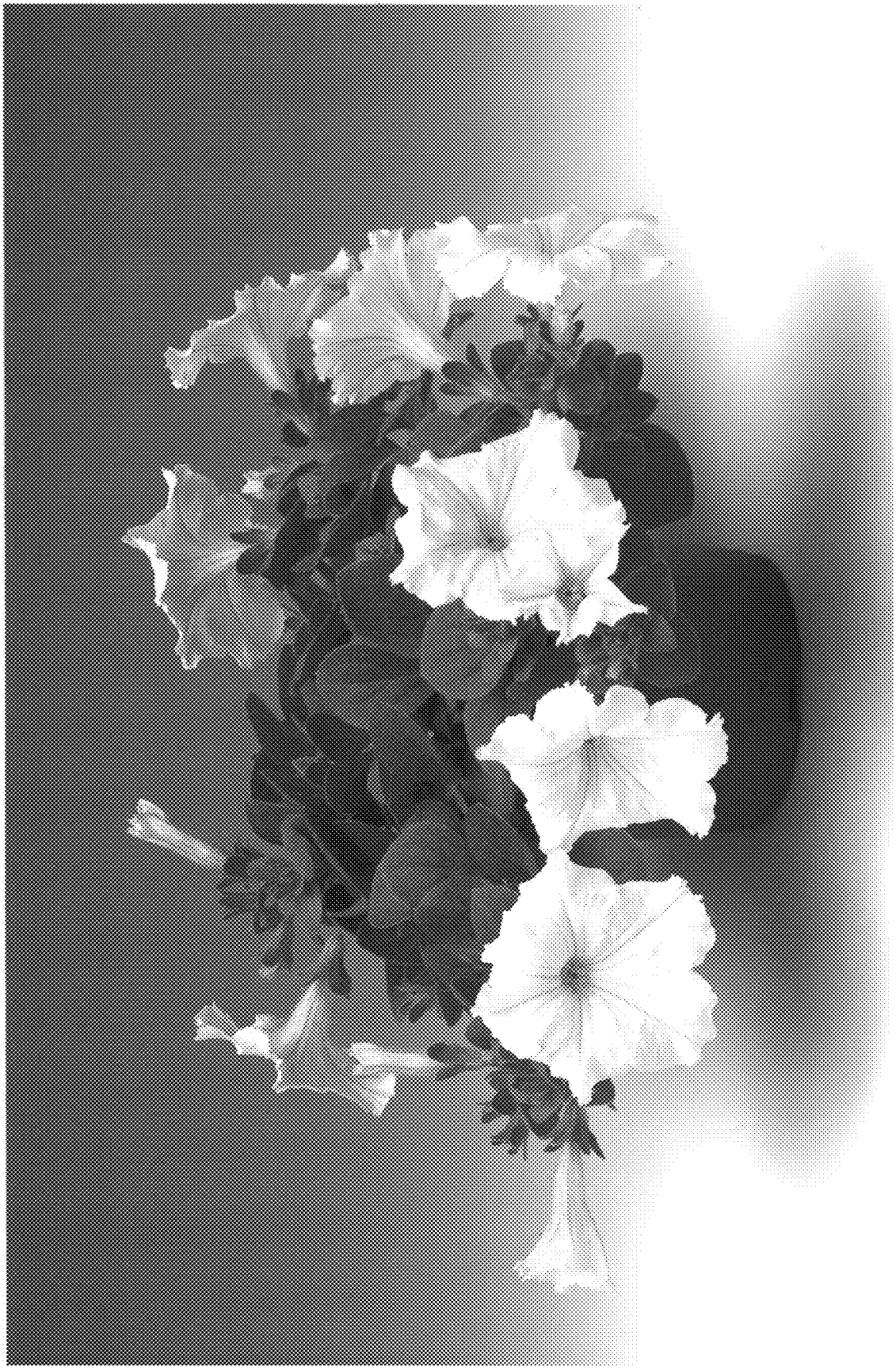

UNITED STATES PATENT AND TRADEMARK OFFICE

CERTIFICATE OF CORRECTION

PATENT NO. : PP 20,946 P2
APPLICATION NO. : 12/321673
DATED : April 27, 2010
INVENTOR(S) : van Kleinwee It is certified that error appears in the above-identified patent and that said Letters Patent is hereby corrected as shown below:

At column 3, line 4, delete "B30896-1," and insert therefor --B0896-1,--

Signed and Sealed this

Fifteenth Day of June, 2010

David J. Kappos

David J. Kappos
*Director of the United States Patent and Trademark Office*